(12) United States Patent
Shiokawa et al.

(10) Patent No.: US 7,045,516 B1
(45) Date of Patent: May 16, 2006

(54) BENZOXAZOLE DERIVATIVES AND DRUGS CONTAINING THE SAME AS THE ACTIVE INGREDIENT

(75) Inventors: Sojiro Shiokawa, Yokohama (JP); Yasuo Sato, Yokohama (JP); Masaaki Izumi, Yokohama (JP); Satoshi Yoshida, Yokohama (JP); Tomoko Ito, Yokohama (JP); Tetsutaro Niisato, Yokohama (JP); Hiroshi Murakami, Kawasaki (JP)

(73) Assignee: Koichi Shudo, Tokyo (JP)

( * ) Notice: Subject to any disclaimer, the term of this patent is extended or adjusted under 35 U.S.C. 154(b) by 0 days.

(21) Appl. No.: 09/856,372

(22) PCT Filed: Nov. 19, 1999

(86) PCT No.: PCT/JP99/06491

§ 371 (c)(1),
(2), (4) Date: Nov. 2, 2001

(87) PCT Pub. No.: WO00/31073

PCT Pub. Date: Jun. 2, 2000

(30) Foreign Application Priority Data

Nov. 20, 1998 (JP) ............................. 10/331274

(51) Int. Cl.
*A61P 1/00* (2006.01)
*A61K 31/55* (2006.01)
*C07D 243/08* (2006.01)

(52) U.S. Cl. ...................... 514/218; 540/575
(58) Field of Classification Search ................ 514/218; 540/575
See application file for complete search history.

(56) References Cited

U.S. PATENT DOCUMENTS 6,037,342 A * 3/2000 Sato et al. ................. 514/218

2003/0013730 A1 * 1/2003 Sato et al. ................. 514/293

FOREIGN PATENT DOCUMENTS

EP 0 621 271 A1 10/1994
EP 806419 11/1997

OTHER PUBLICATIONS

European Search Report dated Nov. 5, 2001.
International Search Report Jan. 11, 2000.
Sato Yasuo et al., "Benzoxazole derivatives as novel 5-HT3 receptor partial agonists in the gut", J.Med. Chem., (1998), 41(16), p. 3015-21.

* cited by examiner

*Primary Examiner*—Brenda Coleman
(74) *Attorney, Agent, or Firm*—Sughrue Mion, PLLC

(57) ABSTRACT

A compound represented by the following general formula (1):

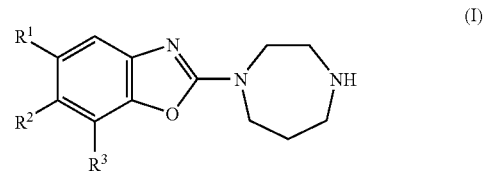

(I)

wherein $R^1$ represents a halogen atom, $R^2$ represents hydrogen atom or a lower alkyl group, and $R^3$ represents hydrogen atom, a lower alkyl group, a lower alkoxyl group, a hydroxy lower alkyl group, a halogen atom, or a substituted or unsubstituted amino group, wherein a substituent on the amino group is selected from the group consisting of a lower alkyl group, a lower alkenyl group, a lower alkylcarbonyl group, and an amino protective group, or a salt thereof. The compound of the present invention or a salt thereof is useful as an active ingredient of medicaments for preventive and/or therapeutic treatment of conditions of irritable bowel syndrome and digestive tract functional disorder, or condition of diarrhea.

5 Claims, No Drawings

BENZOXAZOLE DERIVATIVES AND DRUGS CONTAINING THE SAME AS THE ACTIVE INGREDIENT

This application is a national stage entry under 35 U.S.C. § 371 of PCT/JP99/06491, filed on Nov. 19, 1999.

TECHNICAL FIELD

The present invention relates to benzoxazole derivatives and salts thereof which have serotonin 5-HT$_3$ receptor antagonistic activity and serotonin 5-HT$_3$ receptor partial activating action. The present invention also relates to medicaments which comprise the aforementioned benzoxazole derivatives or pharmaceutically acceptable salts thereof, and are useful for preventive and/or therapeutic treatment of conditions of irritable bowel syndrome, digestive tract functional disorder, or diarrhea, and as an antiemetic agent.

BACKGROUND ART

Serotonin [5-hydroxytryptamine (hereinafter occasionally abbreviated as "5-HT")] is a neurotransmitter in living bodies, and it has been known that there exist seven kinds of subtypes thereof (5-HT$_1$ to 5-HT$_7$). Among them, 5-HT$_3$ receptor has been elucidated to be involved in nausea and vomition as the side effects of carcinostatic agents such as cisplatin and radiotherapy, and 5-HT$_3$ receptor antagonists have been clinically used as antiemetic agents. Specifically, examples include Granisetron [Sanger, G. J. et al., Eur. J. Pharmacol., 159, 113–124 (1989)], Ondansetron (GR38032F) [Butler, A. et al., Br. J. Pharmacol., 94, 387–412 (1988)], and Tropisetron [Richardson, B. P. et al., Nature, 316, 136–131 (1985)]. It has recently been reported that compounds having 5-HT$_3$ receptor antagonistic activity are effective for preventive and/or therapeutic treatment of irritable bowel syndrome and the like [Greenshaw, A. J. et al., Drugs, 53, 20–39 (1997), and Greenshaw, A. J. et al., Trends Pharmacol. Sci., 14, 265–270 (1993)], and development of Alosetron is presently attempted (Japanese Patent Publication (KOKAI) No. 1-151578/1989).

However, when a compound having only the 5-HT$_3$ receptor antagonistic activity is administered to the digestive tract as a preventive and/or therapeutic medicament for irritable bowel syndrome or digestive tract functional disorder, the administration may likely cause a problem of constipation as a side effect, although diarrhea is inhibited. As one of the means for solving this problem, the inventors of the present invention provided benzoxazole derivatives which have 5-HT$_3$ receptor activating action in addition to the 5-HT$_3$ receptor antagonistic activity (Japanese Patent Publication (KOKAI) No. 10-29987/1998). As compounds which similarly have both of the 5-HT$_3$ receptor antagonistic activity and the 5-HT$_3$ receptor activating action, MKC-733 (Japanese Patent Publication (KOKAI) No. 5-310747/1993) and RS-056812-198 [J. A. VanHooft et al., Eur. J. Pharmacol., 322, 229–233 (1997)], are also disclosed.

No compound is reported which exhibits potent inhibitory action against diarrhea without causing the side effect of constipation and is not easily metabolized in living bodies, when it is used as preventive and/or therapeutic medicaments for irritable bowel syndrome or digestive tract functional disorder. Therefore, it has been desired to develop compounds having such characteristic features.

DESCRIPTION OF THE INVENTION

An object of the present invention is to provide a compound useful as an active ingredient of medicaments such as those for preventive and/or therapeutic treatment of conditions resulting from irritable bowel syndrome and digestive tract functional disorder (in particular, defecation abnormalities, abdominal pain, abdominal discomfort, borborygmus, belching, heartburn etc.) and condition of diarrhea, as well as antiemetic agents. More specifically, the object of the present invention is to provide a compound useful as an active ingredient of medicaments, which has the 5-HT$_3$ receptor activating action in addition to the 5-HT$_3$ receptor antagonistic activity, and is hardly metabolized in living bodies, in order to avoid constipation caused as a side effect by the administration of a compound having only the 5-HT$_3$ receptor antagonistic activity as an digestive organ function controlling agent.

The inventors of the present invention already found benzoxazole derivatives having the 5-HT$_3$ receptor activating action in addition to the 5-HT$_3$ receptor antagonistic activity (Japanese Patent Publication (KOKAI) No. 10-29987/1998). They continued keen researches, and found that the compounds represented by the following general formula (1) have the aforementioned characteristics. The present invention was thus achieved.

The inventors of the present invention conducted various tests on the benzoxazoles represented by the following general formula (1), including in vitro metabolic test in human livers and safety test (reverse mutation test), as well as experiments for evaluations of guinea pig extracted ileum constricting action which serves as an index of the 5-HT$_3$ receptor activating action, inhibitory action for diarrhea in rats caused by stress loading which serves as an index of therapeutic treatment of diarrhea, and determination of effect on normal mouse defecation (large bowel transportation ability) which serves as an index of obviation of constipation as the side effect. As a result, they found that the compounds had remarkably higher 5-HT$_3$ receptor antagonistic activity and 5-HT$_3$ receptor activating action as compared with the compounds already disclosed in Japanese Patent Publication (KOKAI) No. 6-345744/1994, and gave more excellent results in in vitro tests, i.e., inhibitory action against diarrhea and effect on normal mouse defecation (large bowel transportation ability) as compared with the compounds already disclosed in Japanese Patent Publication (KOKAI) No. 10-29987/1998, as well as more excellent metabolism stability.

Thus, the present invention provides compounds represented by the following general formula (1) or salts thereof:

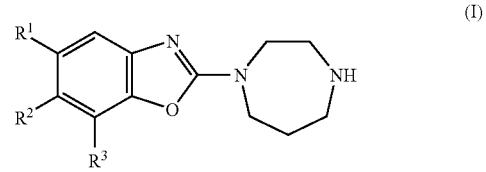

wherein $R^1$ represents a halogen atom, $R^2$ represents hydrogen atom or a lower alkyl group, and $R^3$ represents hydrogen atom, a lower alkyl group, a lower alkoxyl group, a hydroxy lower alkyl group, a halogen atom, or a substituted or unsubstituted amino group, wherein said substituent(s) on the amino group is(are) selected from the group consisting of a lower alkyl group, a lower alkenyl group, a lower alkylcarbonyl group, and an amino protective group.

According to preferred embodiments of the present invention, there are provided the compounds represented by the general formula (1) or salts thereof wherein $R^1$ is chlorine atom; the compounds represented by the general formula (1) or salts thereof wherein $R^2$ is hydrogen atom or methyl group, preferably hydrogen atom; and the compounds represented by the general formula (1) or salts thereof wherein $R^3$ is hydrogen atom, a lower alkyl group, a lower alkoxyl group, a halogen atom, or a substituted amino group, more preferably hydrogen atom, methyl group, ethyl group, methoxy group, chlorine atom, or acetamino group, further preferably a lower alkyl group, and most preferably methyl group.

According to another preferred embodiment of the present invention, there are provided the compounds represented by the general formula (1) or salts thereof wherein $R^1$ is a halogen atom, $R^2$ is hydrogen atom or a lower alkyl group, and $R^3$ is hydrogen atom, a lower alkyl group, a lower alkoxyl group, a halogen atom, or a substituted amino group. As a more preferred embodiment, the present invention provides the compounds represented by the general formula (1) or salts thereof wherein $R^1$ is chlorine atom, $R^2$ is hydrogen atom or methyl group, and $R^3$ is hydrogen atom, methyl group, ethyl group, methoxy group, chlorine atom, or acetamino group.

As further preferred embodiments of the present invention, the following compounds and salts thereof are provided:
5-chloro-2-(1-homopiperazinyl)-7-methylbenzoxazole;
5-chloro-2-(1-homopiperazinyl)-7-methoxybenzoxazole;
5-chloro-2-(1-homopiperazinyl)-6-methylbenzoxazole;
5-chloro-7-ethyl-2-(1-homopiperazinyl)benzoxazole;
5-chloro-2-(1-homopiperazinyl)-7-hydroxymethylbenzoxazole;
7-acetamino-5-chloro-2-(1-homopiperazinyl)benzoxazole;
7-(tert-butyloxycarbonylamino)-5-chloro-2-(1-homopiperazinyl)benzoxazole;
7-amino-5-chloro-2-(1-homopiperazinyl) benzoxazole;
5,7-dichloro-2-(1-homopiperazinyl)benzoxazole;
5,7-dichloro-2-(1-homopiperazinyl)-6-methylbenzoxazole;
5-chloro-2-(1-homopiperazinyl)-6,7-dimethylbenzoxazole;
7-(benzylamino)-5-chloro-2-(1-homopiperazinyl)benzoxazole;
5-chloro-7-ethylamino-2-(1-homopiperazinyl)benzoxazole;
5-chloro-7-methanesulfonylamino-2-(1-homopiperazinyl) benzoxazole;
7-benzoylamino-5-chloro-2-(1-homopiperazinyl)benzoxazole; and
5-chloro-7-isobutyrylamino-2-(1-homopiperazinyl) benzoxazole.

As a particularly preferred embodiment, 5-chloro-2-(1-homopiperazinyl)-7-methylbenzoxazole or a salt thereof is provided.

As another aspect of the present invention, there are provided medicaments which comprise, as an active ingredient, a substance selected from the group consisting of compounds represented by the aforementioned general formula (1), pharmaceutically acceptable salts thereof, and hydrates thereof and solvates thereof. These medicaments are useful for preventive and/or therapeutic treatment of conditions resulting from irritable bowel syndrome and digestive tract functional disorder (in particular, defecation abnormalities, abdominal pain, abdominal discomfort, borborygmus, belching, heartburn etc.) and condition of diarrhea, as well as antiemetic agents and the like. According to preferred embodiments of these medicaments, the aforementioned medicaments are provided in the form of pharmaceutical compositions comprising the aforementioned substance as an active ingredient together with one or more pharmaceutical additives.

As a further aspect of the present invention, there is provided use of a substance selected from the group consisting of compounds represented by the aforementioned general formula (1) and pharmaceutically acceptable salts thereof, and hydrates thereof and solvates thereof for the manufacture of the aforementioned medicaments. According to the present invention, there are further provided methods for preventive and/or therapeutic treatment of conditions resulting from irritable bowel syndrome and digestive tract functional disorder or condition of diarrhea, which comprise a step of administering a preventively and/or therapeutically effective amount of a substance selected from the group consisting of compounds represented by the aforementioned general formula (1) and pharmaceutically acceptable salts thereof, and hydrates thereof and solvates thereof to a mammal including human, preferably human.

As still further aspects of the present invention, there are provided serotonin 5-HT$_3$ receptor antagonistic agents which comprise a substance selected from the group consisting of compounds represented by the aforementioned general formula (1) and pharmaceutically acceptable salts thereof, and hydrates thereof and solvates thereof, and serotonin 5-HT$_3$ receptor partial activators which comprise a substance selected from the group consisting of compounds represented by the aforementioned general formula (1) and pharmaceutically acceptable salts thereof, and hydrates thereof and solvates thereof.

BEST MODE FOR CARRYING OUT THE INVENTION

In the present specification, an alkyl group or an alkyl moiety of a substituent containing the alkyl moiety may be linear, branched, cyclic or a combination thereof, and preferably means a linear or branched alkyl group. The term "lower" used herein means that a substituent has about 1 to 4 carbon atoms (2 to 4 carbon atoms for alkenyl groups and the like). Examples of the lower alkyl group or alkyl moieties of substituents containing the same include methyl group, ethyl group, n-propyl group, isopropyl group, cyclopropyl group, n-butyl group, sec-butyl group, isobutyl group, tert-butyl group, cyclopropylmethyl group and the like. The term "halogen atom" used herein means any one of fluorine atom, chlorine atom, bromine atom, and iodine atom.

As the substituent (s) of the amino group represented by $R^3$, a group selected from the groups consisting of a linear or branched $C_1$–$C_4$ alkyl group, a linear or branched $C_2$–$C_4$ alkenyl group, a linear or branched $C_1$–$C_4$ alkyl carbonyl group, and groups described in T. W. Green, "Protecting Group inorganic Synthesis", John Wiley and Sons, 1991 as protective groups for amino group may preferably be used.

$R^1$ is preferably chlorine atom. $R^2$ is preferably hydrogen atom or methyl group, and more preferably hydrogen atom. $R^3$ is preferably a lower alkyl group, and more preferably methyl group.

Examples of the compounds of the present invention include the following compounds:
5-chloro-2-(1-homopiperazinyl)-7-methylbenzoxazole;
5-chloro-2-(1-homopiperazinyl)-7-methoxybenzoxazole;
5-chloro-2-(1-homopiperazinyl)-6-methylbenzoxazole;

5-chloro-7-ethyl-2-(1-homopiperazinyl)benzoxazole;
5-chloro-2-(1-homopiperazinyl)-7-hydroxymethylbenzoxazole;
7-acetamino-5-chloro-2-(1-homopiperazinyl)benzoxazole;
7-(tert-butyloxycarbonylamino)-5-chloro-2-(1-homopiperazinyl) benzoxazole;
7-amino-5-chloro-2-(1-homopiperazinyl)benzoxazole;
5,7-dichloro-2-(1-homopiperazinyl)benzoxazole;
5,7-dichloro-2-(1-homopiperazinyl)-6-methylbenzoxazole;
5-chloro-2-(1-homopiperazinyl)-6,7-dimethylbenzoxazole;
7-(benzylamino)-5-chloro-2-(1-homopiperazinyl) benzoxazole;
5-chloro-7-ethylamino-2-(1-homopiperazinyl) benzoxazole;
5-chloro-7-methanesulfonylamino-2-(1-homopiperazinyl) benzoxazole;
7-benzoylamino-5-chloro-2-(1-homopiperazinyl) benzoxazole; and
5-chloro-7-isobutyrylamino-2-(1-homopiperazinyl) benzoxazole. However, the compounds of the present invention are not limited to these examples.
Preferred compounds include:

acid, hydrogen peroxide acid, and carbonic acid; organic carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid; acidic amino acid such as aspartic acid and glutamic acid; alkylsulfonic acid or arylsulfonic acid such as methanesulfonic acid and p-toluenesulfonic acid and the like.

The compounds of the present invention may have one or more asymmetric carbons depending on the types of the substituents. Optically active substances and diastereoisomers based on the presence of one or more asymmetric carbons, any mixtures thereof, racemates thereof and the like fall within the scope of the present invention. The compounds of the present invention or salts thereof may also exist as a hydrate or a solvate. Furthermore, any substances in any crystal forms also fall within the scope of the present invention.

The compounds of the present invention may be produced by various methods. For example, they are produced by the following two typical methods (Method A and Method B).

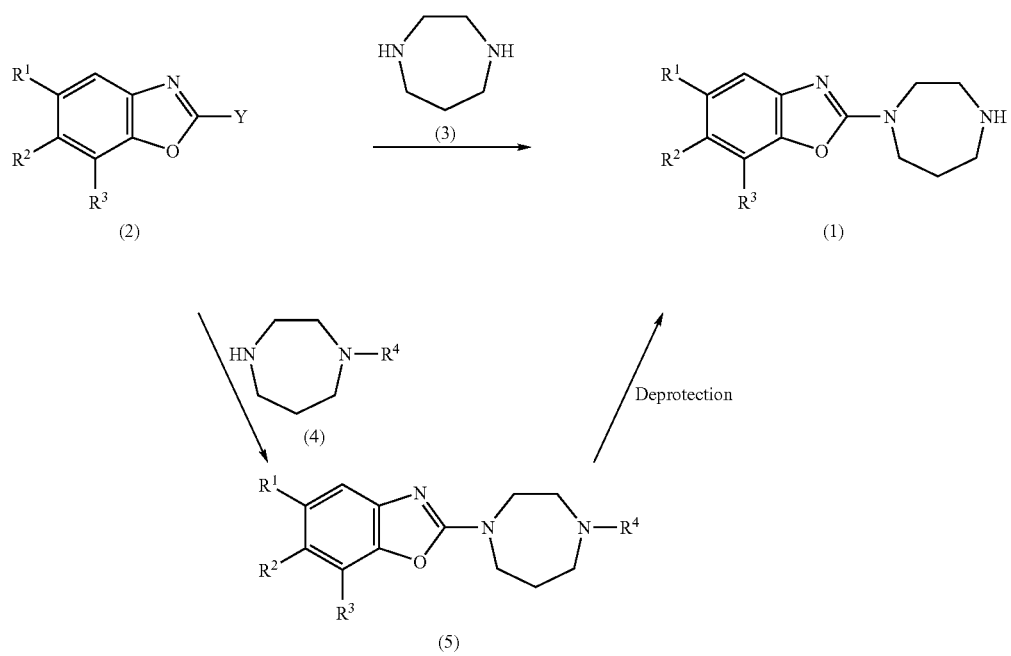

5-chloro-2-(1-homopiperazinyl)-7-methylbenzoxazole;
5-chloro-2-(1-homopiperazinyl)-7-methoxybenzoxazole;
5-chloro-2-(1-homopiperazinyl)-6-methylbenzoxazole;
5-chloro-7-ethyl-2-(1-homopiperazinyl)benzoxazole;
5-chloro-2-(1-homopiperazinyl)-7-hydroxymethylbenzoxazole;
and 7-acetamino-5-chloro-2-(1-homopiperazinyl)benzoxazole:
and a most preferred compound is 5-chloro-2-(1-homopiperazinyl)-7-methylbenzoxazole.

The compounds of the present invention represented by the formula (1) may exist in the form of a free base or in the form of an acid addition salt. Examples of the salt include salts with a hydrohalogenic acid such as hydrofluoric acid, hydrochloric acid, hydrobromic acid and hydroiodic acid; inorganic acid such as sulfuric acid, nitric acid, phosphoric In the scheme, $R^1$, $R^2$ and $R^3$ have the same meanings as those defined above, Y represents a leaving group such as a halogen atom, thiol group, p-toluenesulfonyl group, or trifluoromethanesulfonyl group, and $R^4$ represents a protective group for amino group.

Method A:

A compound of the formula (1) can be obtained by reacting a compound of the formula (2) with homopiperazine of the formula (3) in a solvent. The solvent may be dichloromethane, chloroform, benzene, toluene, xylene, tetrahydrofuran, diethyl ether, dimethoxyethane, N,N-dimethyl formamide, dimethylsulfoxide or the like. A reaction temperature can be selected from a range of −50 to 200° C., preferably 0 to 150° C., and the reaction is performed for 5 minutes to 48 hours, preferably 30 minutes to 20 hours. In order to accelerate the reaction, or to perform the reaction under a mild condition, an additive (e.g., triethylamine) may be added to the reaction system.

Method B:

A compound of the formula (5) can be obtained by reacting a compound of the formula (2) in a solvent with homopiperazine of the formula (4) in which one of the amino groups is protected. The protective group for amino group may be selected from, for example, those described in T. W. Green, "Protecting Group in Organic Synthesis", John Wiley and Sons, 1991. The solvent, reaction temperature, reaction time, and additives may be similar to those mentioned for Method A. Then, a compound of the formula (1) is obtained by eliminating R4 as the protective group by an appropriate method.

The compounds of the formulas (1) or (5) produced by Method A or Method B may be subjected to conversion of a functional group on the substituent $R^1$, $R^2$ or $R^3$ to prepare different compounds that fall within the scope of the present invention.

The compounds represented by the aforementioned general formula (1) have advantages in that they show the 5-$HT_3$ receptor antagonistic activity and the 5-$HT_3$ receptor activating action, and they are hardly metabolized in human livers. Therefore, the compounds represented by the formula (1) can be used as an active ingredient of medicaments, as a 5-$HT_3$ receptor antagonist and 5-$HT_3$ receptor activator, for preventive and/or therapeutic treatment of diseases in which 5-$HT_3$ participates. The diseases in which 5-$HT_3$ participates include irritable bowel syndrome, digestive tract functional disorder, headache, neuralgia, anxiety, depression, mental diseases, or vomition caused by carcinostatic agents such as cisplatin or radiotherapy. Since the compounds represented by the formula (1) have partial activating action on 5-$HT_3$ receptor exhibited as the 5-$HT_3$ receptor activating action in addition to the 5-$HT_3$ receptor antagonistic activity, they are also useful as a preventive medicament or therapeutic medicament without causing the side effect of constipation for improving conditions of irritable bowel syndrome, digestive tract functional disorder, or diarrhea, or as an antiemetic agent.

As the active ingredient of the medicaments of the present invention, a substance selected from the group consisting of the aforementioned compounds in free form, pharmaceutically acceptable non-toxic salts thereof, and hydrates thereof and solvates thereof can be used. The medicaments of the present invention can be administered to human as well as mammals other than human. The present invention also provides pharmaceutical compositions which comprise one or more kinds of substances selected from the group consisting of the aforementioned compounds in free form, pharmaceutically acceptable salts thereof, and hydrates thereof and solvates thereof, together with one or more kinds of pharmaceutical additives, and are suitable for either oral administration or parenteral administration.

More specifically, examples of the pharmaceutical compositions suitable for oral administration include, for example, tablets, capsules, pills, powders, granules, subtilized granules, syrups, emulsions, suspensions, solutions, aqueous solutions and the like. Examples of the pharmaceutical compositions suitable for parenteral administration include, for example, injections such as intravenous, intramuscular or subcutaneous injections, implants, suppositories for rectal administration, ointments, emplastrums, adhesive tapes for transdermal absorption and the like. The injections may be added with buffering agents (e.g., acetate, citrate, phosphate), pH modifiers (e.g., sodium hydrogencarbonate, sodium hydroxide, hydrochloric acid), stabilizing agents such as antioxidants (e.g., ascorbic acid, sodium sulfite, sodium pyrosulfite), preservatives (e.g., benzyl alcohol, chlorobutanol, p-hydroxybenzoic acid methyl ester, phenol) and the like, if required. These pharmaceutical preparations can be produced by conventional methods using ordinarily used pharmaceutical additives such as excipients, disintegrating agents, binders, lubricants, colorants and the like.

Examples of usable non-toxic excipients include, for example, lactose, glucose, cornstarch, sorbitol, crystalline cellulose and the like. Examples of disintegrator include, for example, starch, sodium alginate, gelatin, calcium carbonate, dextrin and the like. Examples of binders include, for example, dimethylcellulose, polyvinyl alcohol, polyvinyl ether, methylcellulose, ethylcellulose, gum arabic, hydroxypropylcellulose, polyvinylpyrrolidone and the like. Examples of lubricants include, for example, talc, magnesium stearate, polyethylene glycol, hardened oil and the like. Examples of colorants include, for example, Brilliant Blue, erythrosine, Tartrazine and the like.

The compounds represented by the formula (1) according to the present invention may also be administered in combination with other therapeutic medicaments. For example, when used for treatment of irritable bowel syndrome, the compounds of the present invention may be used in combination with opioids (Loperamide, Trimebutine and the like), anti-choline agents (Prifinium Bromide, Tiquizium Bromide and the like), dopamine antagonists (Domperidone, Sulpiride and the like), antiflatuents, anti-anxiety agents (benzodiazepine medicaments and the like), anti-depression agents (Desipramine, Amitriptyline, Tripramine and the like) and the like. For the control of digestive organ functions, or treatment of gastrointestinal motility disorders, nausea and vomition, the compounds represented by the formula (1) according to the present invention may appropriately be used in combination with histamine $H_2$ receptor antagonists (Cimetidine, Ranitidine, Famotidine, Sufotidine, Nizatidine, Roxatidine and the like), anti-secretion agents ($H^+K^+$ ATPase inhibitors such as Omeprazole) and the like.

The content of the compounds of the present invention in pharmaceutical compositions may vary depending on a dosage form, and may usually be about 0.05 to 50% by weight, preferably 0.1 to 20% by weight of the weight of the compositions.

The dose may be appropriately chosen by individually considering the age, body weight, sexuality of a patient, nature of a disease, severity of conditions and the like. However, when the compounds are used as prophylactic or therapeutic agent for the treatment of irritable bowel syndrome or digestive tract functional disorder, they are usually administered in an amount of 0.001 to 100 mg, preferably 0.01 to 50 mg/unit dose as active ingredient per day for adults once in a day or at several times as divided portions.

EXAMPLES

The present invention will be explained in detail with reference to the following examples. However, the descriptions are only given as examples, and do not limit the present invention. It should be understood that various alterations and modifications are possible without departing from the scope of the present invention.

The NMR data mentioned in the examples were obtained by a 400 MHz NMR spectrometer, and data are shown as d values using TMS as a standard. Methods for producing raw materials used in the examples and control compounds for evaluation are shown in Reference Examples.

Reference Example 1

5-Chloro-2-mercapto-7-methoxybenzoxazole

(a) 4-Chloro-2-methoxyphenol

2-Methoxyphenol (5.0 g), 2-aminopyridine (0.3 g), and thionyl chloride (3.24 mL) were stirred at 70° C. in toluene (100 mL) for 19 hours. The reaction mixture was cooled to room temperature, and then the solvent was evaporated under reduced pressure to obtain the title compound as an oil (6.6 g).

$^1$H-NMR (CDCl$_3$) δ: 3.86 (3H, s), 5.20 (1H, br), 6.83 (3H, m)
MS (EI): m/z 158 (M$^+$)

(b) 4-Chloro-2-nitro-6-methoxyphenol

4-Chloro-2-methoxyphenol (1.77 g) was dissolved in acetic acid (18 mL). To this solution, a separately prepared nitric acid solution (mixture of 70% nitric acid (1.88 mL) and acetic acid (5 mL)) was added under ice cooling with stirring. The mixture was stirred at room temperature for 1 hour, diluted with ethyl acetate, and washed with water. The ethyl acetate layer was dried over anhydrous magnesium sulfate, and then the solvent was evaporated under reduced pressure to obtain a crude product. This product was purified by silica gel chromatography (ethyl acetate:n-hexane=4:1 v/v) to obtain the title compound (1.8 g).

$^1$H-NMR (CDCl$_3$) δ: 3.95 (3H, s), 7.10 (1H, d, J=3.0 Hz), 7.70 (1H, d, J=3.0 Hz)
MS (TPS): m/z 203 (M$^+$)

(c) 5-Chloro-2-mercapto-7-methoxybenzoxazole

Under argon flow, platinum on sulfide carbon (0.18 g) was suspended in a solution of 4-chloro-2-nitro-6-methoxyphenol (1.77 g) in ethyl acetate (17 mL). Inside of the reaction system was replaced with hydrogen gas, and the suspension was stirred vigorously for 24 hours. The platinum on sulfide carbon was removed by filtration using Celite, and then the solvent was evaporated under reduced pressure. The resultant crude product was dissolved in ethanol (30 mL), and the mixture was added with carbon disulfide (15 mL) and potassium hydroxide (0.58 g), and the mixture was stirred at 60 C.° for 3 hours. The reaction mixture was cooled to room temperature, added with water (30 mL), and adjusted to pH 4 with concentrated hydrochloric acid. The deposited solid was collected by filtration, and dried at 4 C.° under reduced pressure for 5 hours to obtain the title compound (1.87 g).

$^1$H-NMR (CD$_3$OD) δ: 3.88 (3H, s), 6.72 (1H, d, J=2.0 Hz), 6.82 (1H, d, J=2.0 Hz)
MS (TPS): m/z 216 (M$^+$+1)

Reference Example 2

5-Chloro-7-hydroxymethyl-2-mercaptobenzoxazole

(a) 5-Chloro-3-nitrosalicylic acid ethyl ester

A solution of 5-chlorosalicylic acid (5.0 g) in ethanol (50 mL) was added with concentrated sulfuric acid (2.0 mL), and heated under reflux for 24 hours. After the ethanol was evaporated under reduced pressure, the resultant oil was dissolved in ethyl acetate, and the solution was washed with saturated aqueous solution of sodium hydrogencarbonate. The ethyl acetate layer was washed successively with water and saturated brine, and dried over anhydrous magnesium sulfate. Then, the solvent was evaporated under reduced pressure to obtain roughly purified 5-chlorosalicylic acid ethyl ester (5.3 g). This product was treated with 70% nitric acid (7.2 mL, d=1.42) in acetic anhydride (40 mL) under ice cooling. The reaction mixture was stirred at the same temperature for 6 hours, and poured into iced water, and the deposited crystals were collected by filtration. The crystals were washed with water, and dried under reduced pressure to obtain the title compound (1.48 g).

$^1$H-NMR (CDCl$_3$) δ: 1.39 (3H, t, J=7.1 Hz), 4.42 (2H, q, J=7.1 Hz), 8.03 (1H, d, J=2.7 Hz), 8.07 (1H, d, J=2.7 Hz), 11.93 (1H, s)

(b) 5-Chloro-7-ethoxycarbonyl-2-mercaptobenzoxazole

5-Chloro-3-nitrosalicylic acid ethyl ester (1.0 g) was dissolved in a mixture of ethyl acetate (10 mL) and ethanol (10 mL), and the mixture was added with platinum on sulfide carbon (100 mg). The mixture was stirred vigorously under hydrogen atmosphere for 20 hours. The platinum on sulfide carbon was removed by filtration using Celite, and the solvent was evaporated under reduced pressure. A solution of the resultant product in carbon disulfide (30 mL) was added with a solution of potassium hydroxide (338 mg) in ethanol (30 mL), and the mixture was heated at 70 C.° for 5 hours. The solvent was evaporated under reduced pressure, and the residue was added with diethyl ether, adjusted to pH 9.0 with 0.5 N aqueous potassium hydroxide, and then extracted. The separated aqueous layer was washed again with diethyl ether, adjusted to pH 5.0 with 1.0 N hydrochloric acid, and extracted 3 times with ethyl acetate. The ethyl acetate layer was dried over anhydrous magnesium sulfate, and the solvent was evaporated under reduced pressure to obtain the title compound (982 mg).

$^1$H-NMR (CDCl$_3$) δ: 1.41 (3H, t, J=7.0 Hz), 3.40 (1H, br), 4.45 (2H, q, J=7.0 Hz), 7.60 (1H, d, J=2.2 Hz), 7.71 (1H, d, J=2.2 Hz)
MS (EI): m/z 257 (M$^+$)

(c) 5-Chloro-7-hydroxymethyl-2-mercaptobenzoxazole

5-Chloro-7-ethoxycarbonyl-2-mercaptobenzoxazole (280 mg) was dissolved in diethyl ether (20 mL), and the mixture was added with lithium tetrahydride borane (100 mg). The mixture was stirred at 35 C.° for 2 hours. The reaction mixture was added with methanol and 1 N hydrochloric acid, and volatile components were evaporated under reduced pressure. This procedure was repeated 3 times. The resultant product was purified by silica gel chromatography (methanol:methylene chloride=1:20) to obtain the title compound (163 mg).

$^1$H-NMR (DMSO-d$_6$) δ: 4.64 (2H, s), 5.53 (1H, br), 7.18 (1H, s), 7.26 (1H, s), 14.0 (1H, br)
MS (EI): m/z 215 (M$^+$)

Reference Example 3

7-Acetamino-5-chloro-2-mercaptobenzoxazole

(a) 2-Acetamino-4-chlorophenol

Under ice cooling, a solution of 2-acetamino-4-chlorophenol (2.0 g, 14 mmol) in methylene chloride (12 mL) was added with triethylamine (3.89 mL) and acetic anhydride (1.5 mL) with stirring. After the mixture was stirred for 30 minutes, the solvent and triethylamine were evaporated under reduced pressure. The resultant reaction mixture was dissolved in diethyl ether, and the mixture was washed successively with saturated aqueous sodium hydrogencarbonate and saturated brine. The organic layer was dried over anhydrous magnesium sulfate, and the solvent was evaporated under reduced pressure to obtain the title compound (2.6 g, 100%).

$^1$H-NMR (CDCl$_3$) δ: 2.20 (3H, s), 6.81 (1H, d, J=8.5 Hz), 6.95 (1H, dd, J=8.6, 2.6 Hz), 7.72 (1H, d, J=2.6 Hz)

(b) 2-Acetamino-4-chloro-6-nitrophenol

Under ice cooling, a solution of 2-acetamino-4-chlorophenol (1.0 g, 5.4 mmol) in acetic anhydride (90 mL) was added with 70% nitric acid (0.38 mL, d=1.42) with stirring. After stirring for 2 hours, the mixture was added with water (100 mL), and the mixture was further stirred for 1 hour. The mixture was extracted by adding diethyl ether, and washed twice with water. The organic layer was dried over anhydrous magnesium sulfate, and the solvent was evaporated under reduced pressure. The resultant mixture was purified by silica gel column chromatography (ethyl acetate:n-hexane=5:1 v/v) to obtain the title compound (0.38 g, 31%).

$^1$H-NMR (CDCl$_3$) δ: 2.28 (3H, s), 7.80 (1H, d, J=2.5 Hz), 8.80 (1H, d, J=2.5 Hz), 10.98 (1H, s)

MS (EI) m/z: 230 (M$^+$)

(c) 7-Acetamino-5-chloro-2-mercaptobenzoxazole

Under argon flow, platinum on sulfide carbon (0.1 g) was suspended in a solution of 2-acetamino-4-chloro-6-nitrophenol (100 mg, 0.43 mmol) in a mixture of ethanol (5 mL) and ethyl acetate (5 mL). Inside of the reaction system was replaced with hydrogen gas, and the mixture was stirred vigorously for 24 hours. After the platinum on sulfide carbon was removed by filtration using Celite, the solvent was evaporated under reduced pressure. The resultant crude product was dissolved in ethanol (5.4 mL), and the solution was added with carbon disulfide (5.4 mL) and potassium hydroxide (0.29 g), and the mixture was then stirred at 60 C.° for 2 hours. The reaction mixture was cooled to room temperature, and volatile components were evaporated under reduced pressure. The resultant reaction mixture was dissolved in ethyl acetate (10 mL), and washed successively with saturated aqueous ammonium chloride (10 mL) and saturated brine. The reaction mixture was dried over anhydrous magnesium sulfate, and the solvent was evaporated under reduced pressure to obtain the title compound (104 mg, 99%).

$^1$H-NMR (CD$_3$OD) δ: 2.11 (3H, s), 6.87 (1H, d, J=1.9 Hz), 7.77 (1H, d, J=1.9 Hz)

MS (EI) m/z: 242 (M$^+$)

Reference Example 4

5-Chloro-7-methyl-2-(1-piperazinyl)benzoxazole

Piperazine (4.3 g, 0.05 mol) was added to a suspension of 5-chloro-2-mercapto-7-methylbenzoxazole (5.0 g, 0.25 mol) in toluene (100 mL) with stirring. The reaction mixture was stirred for 7 hours under reflux, then cooled, and the mixture was added to a mixture of ethyl acetate (45 mL) and water (80 mL). The mixture was adjusted to pH 7.5 by gradually adding 5 N hydrochloric acid. The separated organic layer was washed with water (80 mL), added with water (80 mL) again, and adjusted to pH 1–1.5 with 5 N hydrochloric acid. The organic layer was removed by phase separation. The remaining aqueous layer was added with ethyl acetate, adjusted to pH 8.0 with 5 N aqueous sodium hydroxide, and then extracted. The organic layer was washed with water and saturated brine, and dried over anhydrous magnesium sulfate, and the solvent was evaporated under reduced pressure to obtain the title compound (4.3 g). This compound may be converted into 5-chloro-7-methyl-2-(1-piperazinyl) benzoxazole hydrochloride by treatment with 4 N hydrochloric acid/ethyl acetate in ethyl acetate.

$^1$H-NMR (CDCl$_3$) δ: 1.83 (1H, br), 2.37 (3H, m), 2.99 (4H, m), 3.68 (4H, m), 3.00 (2H, m), 6.81 (1H, J=1.2 Hz), 7.13 (1H, d, J=1.2 Hz)

MS (EI): m/z 252 (M$^+$+1)

Reference Example 5

7-(tert-Butyloxycarbonylamino)-5-chloro-2mercaptobenzoxazole (a) 4-Chloro-2,6-dinitrophenol A solution of 4-chloro-2-nitrophenol (4 g, 23 mmol) in acetonitrile (100 ml) was cooled to −25 C.°, and gradually added with nitronium tetrafluoroborate powder (4.9 g). The reaction mixture was stirred for 2 hours while the temperature was raised to −10 C.°, and the reaction was stopped by adding 10 ml of water. The acetonitrile was evaporated under reduced pressure, and the residue was diluted with diethyl ether. The ether layer was washed with water, then washed twice with saturated brine, and dried over anhydrous magnesium sulfate. The solvent was evaporated by vacuum concentration to obtain the title compound as yellow plate crystals (5.1 g).

$^1$H-NMR (CDCl$_3$) δ: 8.06 (2H, brs)

MS (EI) m/z: 218 (M$^+$)

(b) 2-Amino-4-chloro-6-nitrophenol

The compound of Reference Example 5 (a) (4-chloro-2, 6-dinitrophenol, 5.1 g, 23.7 mmol) was dissolved in anhydrous ethanol (106 ml), and the solution was added with 5 N hydrochloric acid (28.4 ml), and the mixture was gradually added with stannous chloride hydrate (16 g) at 25 C.°. After stirring for 15 minutes, the solvent was evaporated under reduced pressure, and the residue was diluted with n-hexane. The solution was washed twice with water, and dried over anhydrous magnesium sulfate, and the solvent was evaporated under reduced pressure to obtain the title compound as reddish brown powder (2 g).

MS (EI): m/z 188 (M$^+$)

(c) 2-(tert-Butyloxycarbonylamino)-4-chloro-6-nitrophenol

The compound of Reference Example 5 (b) (2-amino-4-chloro-6-nitrophenol, 0.376 g) was dissolved in 1,2-dichloroethane (12 ml), and then the solution was added with triethylamine (3 ml), di-tert-butyl dicarbonate (2 ml), and hydroxylamine hydrochloride (0.07 g). After stirring for 3 hours under reflux, the reaction was stopped by adding water (10 ml). The reaction mixture was diluted with n-hexane (30 ml), and the organic layer was washed with 20 ml of water. The organic layer was dried over anhydrous magnesium sulfate, and the solvent was evaporated under reduced pressure to obtain an oily crude product (1.2 g). The product was purified by silica gel column chromatography (ethyl acetate:n-hexane=5:95) to obtain the title compound as yellow crystals (0.45 g).

$^1$H-NMR (CD$_3$OD) δ: 1.44 (9H, s), 7.63 (1H, m), 8.18 (1H, br)

MS (TSP) m/z: 287 (M$^+$−1)

(d) 7-(tert-Butyloxycarbonylamino)-5-chloro-2-mercaptobenzoxazole

The compound of Reference Example 5 (c) (2-(tert-butyloxycarbonylamino)-4-chloro-6-nitrophenol, 1.0 g) was dissolved in anhydrous ethanol (20 ml), and platinum on sulfide carbon (0.1 g) was suspended in the solution under inert gas flow. The atmosphere was replaced with hydrogen gas at 2 C.°, and the mixture was stirred for about 2 hours. After the reaction was completed, the catalyst was quickly removed by filtration using Celite. The filtrate was added with carbon disulfide (10 ml) and potassium hydroxide (0.97 g), and stirred at 60 C.° for about 2 hours. The reaction mixture was cooled to room temperature, and the solvent was evaporated under reduced pressure. The residue was dissolved in water (20 ml). 1 N hydrochloric acid was added portionwise to the aqueous solution, and the solids deposited when pH was adjusted to 7.0 were collected by filtration, and dried under reduced pressure to obtain the title compound (1.5 g).

$^1$H-NMR (CD$_3$OD) δ: 1.45 (9H, s), 6.78 (1H, d, J=1.9 Hz), 7.03 (1H, d, J=1.9 Hz)

Reference Example 6

5,7-Dichloro-2-mercapto-6-methylbenzoxazole (a) 2,4-Dichloro-3-methyl-6-nitrophenol 1,4-Dichloro-3-methylphenol (5 g) was dissolved in acetic acid (12.5 ml), and the solution was added with concentrated sulfuric acid (d=1.86, 50 ml). The mixture was gradually added with a mixed acid (2.5 ml of 70% nitric acid+10 ml of concentrated sulfuric acids) over 30 minutes or more under ice cooling, then warmed to room temperature, and stirring was continued for about 2 hours. This reaction mixture was poured into iced water (50 ml), and the deposited solids were collected by filtration, and dried to obtain the title compound as reddish yellow solid (5.22 g).

$^1$H-NMR (CDCl$_3$) δ: 8.06 (2H, brs)

MS (EI) m/z: 218 (M$^+$)

(b) 5,7-Dichloro-2-mercapto-6-methylbenzoxazole

The compound of Reference Example 6 (a) (2,4-dichloro-3-methyl-6-nitrophenol, 2.1 g) was dissolved in a mixture of ethanol (40 ml) and ethyl acetate (40 ml), and platinum on sulfide carbon (0.2 g) was suspended in the solution under inert gas flow. The atmosphere was replaced with hydrogen gas at 25 C.°, and the reaction system was maintained for reaction for about 20 hours. The platinum catalyst was removed from the reaction mixture by filtration, and the filtrate was added with anhydrous ethanol (40 ml) and carbon disulfide (20 ml). The mixture was then added with potassium hydroxide (0.6 g), and the mixture was allowed to react at 60 C.° for 8 hours. After the reaction mixture was cooled to room temperature, the solvent was evaporated under reduced pressure, and the residue was dissolved in water (20 ml). This aqueous solution was made weakly acidic (pH=4) by adding hydrochloric acid. The precipitates were collected by filtration, and dried under reduced pressure to obtain the title compound (0.73 g).

$^1$H-NMR (CDCl$_3$) δ: 2.50 (3H, s), 7.15 (1H, s)

MS (EI) m/z: 233 (M$^+$−1)

Reference Example 7

5-Chloro-2-mercapto-6,7-dimethylbenzoxazole (a) 4-Chloro-2,3-dimethyl-6-nitrophenol 2,3-Xylenol (5 g, 40.9 mmol) was dissolved in toluene (100 ml), and the solution was added with 2-aminopyridine (0.3 g, 3.2 mmol). The mixture was added with thionyl chloride (3.3 ml) at room temperature with stirring, and then stirred at 7 C.° for 15 hours. The reaction mixture was cooled to room temperature, and then excessive reagents and solvent were evaporated under reduced pressure to obtain an oily substance. The substance was dissolved in acetic acid (12.5 ml), and the solution was added with concentrated sulfuric acid (50 ml), and then added dropwise with a mixed acid (2.5 ml of 70% nitric acid+10 ml of concentrated sulfuric acid) at room temperature over 30 minutes or more. The mixture was further stirred for 2 hours, and poured into iced water (500 ml). The precipitates were collected by filtration, and dried to obtain a crude product (3.8 g). The product was purified by silica gel column chromatography (n-hexane:ethyl acetate=2:1 v/v) to obtain the title compound (1.5 g).

$^1$H-NMR (CDCl$_3$) δ: 2.18 (3H, s), 2.24 (3H, s), 6.72 (1H, s)

MS (EI) m/z: 201 (M$^+$), 203 (M$^+$+2)

(b) 5-Chloro-2-mercapto-6,7-dimethylbenzoxazole

The compound of Reference Example 7 (a) (4-chloro-2,3-dimethyl-6-nitrophenol, 1.51 g, 7.51 mmol) was dissolved in a mixture of ethanol (15 ml) and ethyl acetate (25 ml), and then platinum on sulfide carbon (0.15 g) was suspended in the solution under inert gas flow. Subsequently, hydrogen gas was substituted for the atmosphere, and the reaction mixture was stirred for 3 hours. The platinum catalyst was removed by filtration, and the resultant solution was added with anhydrous ethanol (40 ml) and carbon disulfide (20 ml), then added with potassium hydroxide (1.24 g), and the mixture was stirred at 6 C.° for 4 hours. The reaction mixture was cooled to room temperature, and then the solvent was evaporated under reduced pressure. The residue was diluted with appropriate amounts of ethyl acetate and 1 N aqueous sodium hydroxide. The aqueous layer of the solution was separated, and made weakly acidic (pH=4) with concentrated hydrochloric acid. The precipitates were collected by filtration, and dried under reduced pressure to obtain the title compound (1.01 g)

$^1$H-NMR (CD$_3$OD) δ: 2.39 (3H, s), 2.43 (3H, s), 7.09 (1H, s)

MS (EI) m/z: 213 (M$^+$), 215 (M$^+$+2)

Reference Example 8

5,7-Dichloro-2-mercaptobenzoxazole 4,6-Dichloro-2-nitrophenol (5 g) was dissolved in a mixture of ethanol (50 ml) and ethyl acetate (100 ml), and platinum on sulfide carbon (0.5 g) was suspended in the solution under inert gas flow. The hydrogen gas was substituted for the atmosphere at 2 C.°, and the suspension was stirred for about 4 hours. The platinum catalyst was removed from the reaction mixture by filtration, and the resultant solution was added with anhydrous ethanol (100 ml), carbon disulfide (50 ml), and potassium hydroxide (1.6 g) successively, and then the mixture was stirred at 6 C.° for about 1 hour. The reaction mixture was cooled to room temperature, and then the solvent was evaporated under reduced pressure. The resultant residue was diluted with appropriate amounts of ethyl acetate and water. The aqueous layer of the solution was adjusted to pH 5 with concentrated hydrochloric acid. The precipitates were collected by filtration, and dried under reduced pressure to obtain the title compound as white solid (4.7 g).

$^1$H-NMR (CDCl$_3$) 67 : 7.09 (1H, m), 7.26 (1H, m)

Example 1

Preparation of 5-chloro-2-(1-homopiperazinyl)-7-methylbenzoxazole, hydrochloride, sulfate, and methanesulfonate thereof (a)
5-Chloro-2-(1-homopiperazinyl)-7-methylbenzoxazole Under nitrogen atmosphere, a suspension of 5-chloro-2-mercapto-7-methylbenzoxazole (70 g, 35 mol) in toluene (1.4 L) was added with homopiperazine (70 g, 0.35 mol) with stirring, and then the mixture was heated under reflux for 3 hours. The reaction mixture was cooled to room temperature, and poured into a mixture of ethyl acetate (0.7 L) and water (0.7 L). The mixture was added dropwise with 6 N hydrochloric acid (55 mL) with stirring to adjust its pH to 7.5. The separated organic layer was washed with water (1.2 L). The remaining organic layer was added with water (1.2 L), and then added dropwise with 6 N hydrochloric acid with stirring to adjust its pH to 1–1.5. The separated aqueous layer was added with ethyl acetate (1.4 L), and then added with 5 N aqueous sodium hydroxide (180 mL) with stirring to adjust its pH to 8.0. The separated organic layer was washed with water (1.4 L), and dried anhydrous magnesium sulfate, and the solvent was evaporated under reduced pressure to obtain the title compound as a crude product (59 g). A solution of the crude product in ethyl acetate (1.2 L) was added with activated carbon (1.5 g), and the mixture was stirred for 30 minutes at room temperature. Then, the activated carbon was removed by filtration, and the solvent was evaporated under reduced pressure. The resultant solid was added with acetonitrile (177 mL), and was dissolved by warming the mixture to 60 C.° with stirring. The resultant uniform solution was left stand for cooling to room temperature over 1 hour, and then further cooled to 5 C.° The deposited crystals were collected by filtration, and dried under reduced pressure at 40 C.° for 4 hours to obtain the title compound (34 g).

mp: 93–94° C.

$^1$H-NMR (CDCl$_3$) δ: 1.81 (1H, s), 1.90 (2H, m), 2.30 (3H, s), 2.90 (2H, t, J=5.6 Hz), 3.00 (2H, m), 3.71 (4H, m), 6.70 (1H, d, J=1.2 Hz), 7.00 (1H, d, J=1.2 Hz)

Elemental analysis: Found (%): C, 58.5; H, 6.1; N, 15.7. Calculated for $C_{13}H_{16}N_3OCl$ (%): C, 58.7; H, 6.1; N, 15.8.

(b)
5-Chloro-2-(1-homopiperazinyl)-7-methylbenzoxazole hydrochloride

5-Chloro-2-(1-homopiperazinyl)-7-methylbenzoxazole (12 g) was dissolved in ethyl acetate (200 mL), and the solution was added dropwise with 4 N hydrochloric acid/ethyl acetate (16.9 mL, Kokusan Kagaku Co., Ltd.) at room temperature with stirring. After the addition, the mixture was stirred for 30 minutes with ice cooling, and the produced colorless precipitates were collected by filtration. The precipitates were dried at 35 C.° under reduced pressure for 4 hours to obtain the title compound (14.5 g).

$^1$H-NMR (D$_2$O) δ: 2.11 (2H, m), 2.16 (3H, s), 3.27 (2H, m), 3.35 (2H, m), 3.68 (2H, m), 3.88 (2H, m), 6.78 (1H, s), 6.90 (1H, s)

(c)
5-Chloro-2-(1-homopiperazinyl)-7-methylbenzoxazole sulfate

A solution of 5-chloro-2-(1-homopiperazinyl)-7-methylbenzoxazole (2.5 g) in ethyl acetate (75 mL) was added dropwise with a separately prepared sulfuric acid/methanol solution [prepared by adding methanol to 95% sulfuric acid (0.53 mL) to a total volume of 12.5 mL] at room temperature with stirring. The mixture was stirred for 1 hour with ice cooling, and the produced colorless precipitates were collected by filtration. The precipitates were dried at 35 C.° under reduced pressure for 5 hours to obtain the title compound (3.3 g).

Example 1 (c)

Alternative Method 1

The compound of Example 1 (a) [5-chloro-2-(1-homopiperazinyl)-7-methylbenzoxazole, 2900 g] was dissolved in 1 N sulfuric acid (5.8 L), and the aqueous solution was added with ethanol (145 L) and ethyl acetate (99 L) successively. The mixture was stirred at 5 C.° overnight, and the deposited product was collected by filtration, and dried in vacuo at 40 C.° for about 6 hours to obtain the title compound as white crystals (3200 g).

Example 1 (c)

Alternative Method 2

A solution in ethyl acetate (13.4 L) of the crude product, obtained from the process of Example 1 (a), containing 5-chloro-2-(1-homopiperazinyl)-7-methylbenzoxazole (824 g) was added with ethanol (20 L), and then added with 2 N aqueous sulfuric acid (2.98 L). The solution was added with ethyl acetate (6.6 L), and stirred at 5 C.° overnight. The deposited precipitate were collected by filtration, and dried in vacuo at 40 C.° to obtain the title compound as white powder (1010 g).

$^1$H-NMR (D$_2$O) δ: 2.19 (2H, m), 2.19 (3H, s), 3.30 (2H, m), 3.41 (2H, m), 3.76 (2H, m), 3.98 (2H, m), 6.89 (1H, s), 6.99 (1H, s)

Elemental analysis: Found (%): C, 40.5; H, 5.5; N, 10.5. Calculated for $C_{13}H_{18}N_3O_5S_1C_1$ (%): C, 42.92; H, 4.99; N, 11.55.

(d)
5-Chloro-2-(1-homopiperazinyl)-7-methylbenzoxazole methanesulfonate

A solution of 5-chloro-2-(1-homopiperazinyl)-7-methylbenzoxazole (2.5 g) in ethyl acetate (75 mL) was added dropwise with a separately prepared methanesulfonic acid/methanol solution [prepared by adding methanol to methanesulfonic acid (0.61 mL) to a total volume of 12.5 mL] at room temperature with stirring. After the addition, the mixture was stirred for 1 hour at room temperature and for 1 hour with ice cooling, and the produced colorless precipitates were collected by filtration. The precipitates were dried under reduced pressure at 4 C.° for 5 hours to obtain the title compound (3.0 g).

$^1$H-NMR (D$_2$O) δ: 2.09 (2H, m), 2.12 (3H, s), 2.66 (3H, m), 3.26 (2H, m), 3.33 (2H, m), 3.64 (2H, m), 3.82 (1H, s), 6.69 (1H, s), 6.82 (1H, s)

Example 2

5-Chloro-2-(1-homopiperazinyl)-7-methoxybenzoxazole

The title compound (127 mg) was obtained from 5-chloro-2-mercapto-7-methoxybenzoxazole (250 mg, 1.16 mmol) and homopiperazine (232 mg) in the same manner as in Example 1 (a).

$^1$H-NMR (CDCl$_3$) δ: 1.95 (2H, m), 2.10 (1H, br), 2.92 (2H, t, J=5.8 Hz), 3.07 (2H, m), 3.0 (2H, m), 3.79 (4H, m), 3.94 (3H, s), 6.58 (1H, d, J=2.0 Hz), 6.96 (1H, d, J=2.0 Hz)

MS (TSP): m/z 282 (M$^+$+1)

Example 3

5-Chloro-2-(1-homopiperazinyl)-6-methylbenzoxazole

The title compound (115 mg) was obtained from 5-chloro-2-mercapto-6-methylbenzoxazole (200 mg, 1.16 mmol) and homopiperazine (200 mg) in the same manner as in Example 1 (a).

$^1$H-NMR (CDCl$_3$) δ: 1.95 (4H, m), 2.39 (3H, s), 2.92 (2H, t, J=5.6 Hz), 3.07 (2H, m), 3.0 (2H, m), 3.78 (4H, m), 7.10 (1H, s), 7.30 (1H, s)

MS (TSP): m/z 266 (M$^+$+1)

Example 4

5-Chloro-7-ethyl-2-(1-homopiperazinyl)benzoxazole

The title compound (177 mg) was obtained from 5-chloro-7-ethyl-2-mercaptobenzoxazole (200 mg, 1.16 mmol) and homopiperazine (188 mg) in the same manner as in Example 1 (a).

$^1$H-NMR (CDCl$_3$) δ: 1.29 (3H, t, J=7.6 Hz), 1.97 (2H, m), 2.10 (1H, br), 2.75 (2H, q, J=8.4 Hz), 2.93 (2H, d, J=5.8 Hz), 3.08 (2H, m), 3.80 (4H, m), 6.81 (1H, d, J=2.0 Hz), 7.14 (1H, d, J=1.9 Hz)

Example 5

5-Chloro-2-(1-homopiperazinyl)-7-hydroxymethylbenzoxazole

The title compound (177 mg) was obtained from 5-chloro-7-hydroxymethyl-6-methylbenzoxazole (20 mg, 0.23 mmol) and homopiperazine (46 mg) in the same manner as in Example 1 (a).

$^1$H-NMR (DMSO-d$_6$) δ: 2.11 (2H, br), 3.22 (2H, br), 3.33 (1H, br), 3.44 (2H, br), 3.77 (2H, m), 3.94 (2H, m); 4.65 (2H, s), 7.05 (1H, s), 7.23 (1H, s), 9.18 (br)

Example 6

7-Acetamino-5-chloro-2-(1-homopiperazinyl)benzoxazole

The title compound (173 mg, 46%) was obtained from the compound of Reference Example 3 (7-acetamino-5-chloro-2-mercaptobenzoxazole, 292 mg, 1.20 mmol) and homopiperazine (482 mg) in the same manner as in Example 1 (a).

$^1$H-NMR (CDCl$_3$) δ: 1.95 (2H, m), 2.25 (3H, s), 2.93 (2H, t, J=5.6 Hz), 3.07 (2H, m), 3.78 (4H, m), 7.08 (1H, br), 7.71 (1H, br)

MS (EI) m/z: 308 (M$_+$)

Example 7

7-(tert-Butyloxycarbonylamino)-5-chloro-2-(1-homopiperazinyl)benzoxazole

The title compound (1.34 g) was obtained from the compound of Reference Example 5 (7-(tert-butyloxycarbonylamino)-5-chloro-2-mercaptobenzoxazole, 1.15 g, 3.82 mmol) and homopiperazine (1.91 mg) in the same manner as in Example 1 (a).

$^1$H-NMR (CDCl$_3$) δ: 1.56 (9H, s), 1.96 (2H, m), 2.93 (2H, m), 3.09 (2H, m), 3.78 (2H, m), 3.81 (2H, m), 6.58 (1H, br), 7.01 (1H, d, J=2 Hz), 7.65 (0.8H, br)

MS (TSP) m/z: 367 (M$^+$+1)

Example 8

7-Amino-5-chloro-2-(1-homopiperazinyl)benzoxazole hydrochloride

The compound of Example 7 (7-(tert-butyloxycarbonylamino)-5-chloro-2-(1-homopiperazinyl) benzoxazole, 0.68 g, 1.87 mmol) was added with 10 ml of N hydrochloric acid, and the mixture was allowed to react at 5 C.° for 1 hour. After excess hydrochloric acid and water were evaporated by vacuum concentration, the residue was suspended in ethanol, and the deposited product was collected by filtration and dried to obtain the title compound as hydrochloride (0.45 g).

$^1$H-NMR (D$_2$O) δ: 2.14 (2H, m), 3.29 (2H, m), 3.41 (2H, m), 3.75 (2H, m), 3.94 (2H, m), 6.67 (1H, d, 2 Hz), 6.81 (1H, d, J=1.9 Hz)

MS (EI) m/z: 266 (M$^+$)

Example 9

5,7-Dichloro-2-(1-homopiperazinyl) benzoxazole

The title compound (0.18 g) was obtained from the compound of Reference Example 8 (5,7-dichloro-2-mercaptobenzoxazole, 0.17 g, 0.59 mmol) and homopiperazine (0.89 g) in the same manner as in Example 1 (a).

$^1$H-NMR (CDCl$_3$) δ: 1.98 (2H, m), 2.95 (2H, m), 3.10 (2H, m), 3.82 (2H, m), 3.83 (2H, m), 6.98 (1H, d, J=1.7 Hz), 7.18 (1H, d, J=1.7 Hz)

Example 10

5,7-Dichloro-2-(1-homopiperazinyl)-6-methylbenzoxazole

The title compound (77 mg) was obtained from the compound of Reference Example 6 (5,7-dichloro-2-mercapto-6-methylbenzoxazole, 90 mg, 0.384 mmol) and homopiperazine (115 mg) in the same manner as in Example 1 (a).

$^1$H-NMR (CDCl$_3$) δ: 1.97 (2H, m), 2.46 (3H, s), 2.94 (2H, m), 3.09 (2H, m), 3.79 (2H, m), 3.82 (2H, m), 7.24 (1H, s)

Example 11

5-Chloro-2-(1-homopiperazinyl)-6,7-dimethylbenzoxazole

The title compound (103 mg) was obtained from the compound of Reference Example 7 (5-chloro-2-mercapto-6,7-dimethylbenzoxazole, 100 mg, 0.468 mmol) and homopiperazine (141 mg) in the same manner as in Example 1 (a).

$^1$H-NMR (CDCl$_3$) δ: 1.95 (2H, m), 2.33 (3H, s), 2.36 (3H, s), 2.92 (2H, m), 3.08 (2H, m), 3.77 (2H, m), 3.80 (2H, m), 7.19 (1H, s)

Example 12

7-(Benzylamino)-5-chloro-2-(1-homopiperazinyl) benzoxazole (a) [7-amino-5-chloro-2-[1-(4-benzyloxycarbonyl) homopiperazinyl]benzoxazole The compound of Example 7 [7-(tert-butyloxycarbonylamino)-5-chloro-2-(1-homopiperazinyl) benzoxazole, 0.2 g, 0.545 mmol] was dissolved in methylene chloride (4 ml), and the mixture was added with triethylamine (0.153 ml), and then with benzyl chloroformate (0.094 ml) at 5 C.° After stirring for about 3 hours, the reaction mixture was added with saturated aqueous sodium hydrogencarbonate (3 ml) to stop the reaction. The solution was diluted with diethyl ether (10 ml) for phase separation. The aqueous layer was extracted with diethyl ether (10 ml). A combined solution of the extract and the above organic layer was added with water (10 ml), and made strongly acidic by addition of 5 N hydrochloric acid. The aqueous layer was separated, and added with diethyl ether (10 ml), and then made basic with 5 N aqueous sodium hydroxide. The organic layer was washed with saturated brine (20 ml), dried over anhydrous magnesium sulfate, and concentrated under reduced pressure to obtain the title compound (282 mg).

(b) 7-(Benzylamino)-5-chloro-2-(1-homopiperazinyl) benzoxazole

A solution of the compound of Example 12 (a) [7-amino-5-chloro-2-[1-(4-benzyloxycarbonyl) homopiperazinyl]benzoxazole, 47 mg, 0.117 mmol] in 1,2-dichloroethane (2 ml) was added with acetic acid (0.067 ml), and the mixture was added with sodium triacetoxyborohydride (50 mg) under ice cooling. After stirring for about 3 hours, the reaction mixture was added with saturated aqueous sodium hydrogencarbonate to stop the reaction, and diluted with ethyl acetate. The organic layer was washed with water, and then dried over anhydrous magnesium sulfate. The solvent was evaporated under reduced pressure to obtain a crude product as an oil (55 mg). The oil was dissolved in methylene chloride (2 ml), and the solution was added with commercially available 1 M solution of boron trichloride in methylene chloride (0.26 ml) at 0° C., and the mixture was stirred for 3 hours. Then, the reaction was stopped by using saturated aqueous sodium hydrogencarbonate. The mixture was diluted with ethyl acetate, and the organic layer was washed with water. The organic layer was dried over anhydrous magnesium sulfate, and then the solvent was evaporated under reduced pressure to obtain the title compound as a crude product. The product was purified by silica gel column chromatography (methylene chloride:methanol=5:1 v/v) to obtain the title compound (7 mg).

$^1$H-NMR (CDCl$_3$) δ: 1.87 (2H, m), 2.86 (2H, m), 2.98 (2H, m), 3.69 (2H, m), 3.70 (2H, m), 4.36 (2H, s), 6.30 (1H, d, J=1.9 Hz), 6.69 (1H, d, J=1.7 Hz), 7.22–7.34 (5H, m)

MS (TSP) m/z: 357 (M$^+$+1)

Example 13

5-Chloro-7-ethylamino-2-(1-homopiperazinyl) benzoxazole

The compound of Example 8 (7-acetamino-5-chloro-2-(1-homopiperazinyl)benzoxazole, 23 mg) was dissolved in THF (2 ml), and the solution was added with aluminum lithium hydride (13 mg) at 0° C., and the solution stirred for about 3 hours. The reaction was stopped with water (1 ml), and the solution was diluted with ethyl acetate. The organic layer was washed with water, dried over anhydrous magnesium sulfate, and the solvent was evaporated under reduced pressure to obtain the title compound (4 mg).

$^1$H-NMR (D$_2$O) δ: 1.15 (3H, t, J=7.3 Hz), 2.14 (2H, m), 3.29 (2H, m), 3.31 (2H, m), 3.40 (2H, m), 3.75 (2H, t, J=5.8 Hz), 3.94 (2H, t, J=501 Hz), 6.85 (1H, d, J=1.7 Hz), 7.02 (1H, d, J=1.4 Hz)

MS (FAB) m/z: 295 (M$^+$+1)

Example 14

5-Chloro-7-methanesulfonylamino-2-(1-homopiperazinyl) benzoxazole (a) 7-Amino-5-chloro-2-[1-(4-tert-butyloxycarbonyl) homopiperazinyl]benzoxazole The compound of Example 8 (7-amino-5-chloro-2-(1-homopiperazinyl)benzoxazole, 0.12 g) was dissolved in methylene chloride (12 ml), and the solution was added with triethylamine (0.25 ml). The solution was cooled with ice, added with di-tert-butyl dicarbonate (0.170 ml), and the mixture was then stirred for about 3 hours. The reaction was stopped by the addition of saturated aqueous sodium hydrogencarbonate (5 ml), and the reaction mixture was diluted with ethyl acetate (20 ml). The organic layer was washed twice with saturated brine (20 ml), and the resultant organic layer was dried over anhydrous magnesium sulfate. The solvent was evaporated under reduced pressure to obtain the title compound as a grayish black oil (0.272 g).

(b) 5-Chloro-7-methanesulfonylamino-2-(1-homopiperazinyl) benzoxazole hydrochloride The compound of Example 14 (a) (7-amino-5-chloro-2-[1-(4-tert-butyloxycarbonyl) homopiperazinyl]benzoxazole, 45 mg, 0.123 mmol) was dissolved in methylene chloride (2 ml), and the solution was added successively with triethylamine (0.052 ml) and methanesulfonyl chloride (0.01 ml) at 0° C. After the reaction mixture was stirred for 3 hours, the reaction was stopped by using saturated aqueous solution of sodium hydrogencarbonate. The reaction mixture was diluted with ethyl acetate, and the organic layer was washed with water, and dried over anhydrous magnesium sulfate.

The solution was added with 4N hydrochloric acid in ethylacetate (1 ml), and the deposited solids were collected by filtration to obtain the title compound (20 mg).

$^1$H-NMR (CD$_3$OD) δ: 2.22 (2H, m), 3.05 (3H, s), 3.35 (2H, m), 3.47 (2H, m), 3.86 (2H, t, J=6.1 Hz), 4.04 (2H, t, J=5.6 Hz), 7.10 (2H, m)

MS (FAB) m/z: 345 (M$^+$+1)

Example 15

7-Benzoylamino-5-chloro-2-(1-homopiperazinyl) benzoxazole hydrochloride

The compound of Example 14 (a) (7-amino-5-chloro-2-[1-(4-tert-butyloxycarbonyl) homopiperazinyl]benzoxazole, 48 mg, 0.130 mmol) was dissolved in methylene chloride (2 ml), and the solution was successively added with triethylamine (0.056 ml) and benzoyl chloride (0.031 ml) at 0° C. After the reaction mixture was stirred for 3 hours, the reaction was stopped by using saturated aqueous solution of sodium hydrogencarbonate. The reaction mixture was diluted with ethyl acetate, and the organic layer was washed with water and dried over anhydrous magnesium sulfate. The solution was added with 4 N hydrochloric acid in ethyl acetate (1 ml), and the deposited solids were collected by filtration to obtain the title compound (20 mg).

$^1$H-NMR (CD$_3$OD) δ: 2.28 (2H, m), 3.42 (2H, m), 3.53 (2H, m), 3.92 (2H, t, J=6.1 Hz), 4.09 (2H, m), 7.25 (1H, d, L=2.0 Hz), 7.37 (1H, d, J=2.0 Hz), 7.55 (2H, t, J=7.3 Hz), 7.64 (1H, t, J=7.5 Hz), 7.98 (2H, m)

MS (FAB) m/z: 371 (M$^+$+1)

Example 16

5-Chloro-7-isobutyrylamino-2-(1-homopiperazinyl) benzoxazole hydrochloride

The compound of Example 14 (a) (7-amino-5-chloro-2-[1-(4-tert-butyloxycarbonyl) homopiperazinyl]benzoxazole, 58 mg, 0.159 mmol) was dissolved in methylene chloride (2 ml), and the solution was successively added with triethylamine (0.067 ml) and isobutyroyl chloride (0.013 ml) at 0° C. After the reaction mixture was stirred for 3 hours, the reaction was stopped by using saturated aqueous solution of sodium hydrogencarbonate. The reaction mixture was diluted with ethyl acetate, and the organic layer was washed with water and dried over anhydrous magnesium sulfate. The solution was added with 4 N hydrochloric acid in ethyl acetate (1 ml), and the deposited solids were collected by filtration to obtain the title compound (45 mg).

$^1$H-NMR (CD$_3$OD) δ: 1.24 (6H, d, J=7.1 Hz), 2.32 (2H, m), 2.79 (1H, m), 3.44 (2H, m), 3.57 (2H, m), 3.94 (2H, m), 4.15 (2H, m), 7.19 (1H, d, J=1.9 Hz), 7.54 (1H, d, J=1.9 Hz)

MS (FAB) m/z: 337 (M$^+$+1)

Formulation Example 1

Preparation of Tablets

Hydrochloride of the compound of Example 1 (3.0 g), lactose (83.0 g), sodium carboxymethylstarch (10.0 g) and hydroxypropylcellulose (3.0 g) were mixed, and the mixture was added with purified water (6.0 g) and kneaded. The mixture was granulated, dried, and sieved for size adjustment. The resultant granules were mixed with magnesium stearate (1.0 g) and compressed into 100-mg tablets to obtain tablets each containing 3.0 mg of hydrochloride of the compound of Example 1.

Formulation Example 2

Preparation of Granules

Sulfate of the compound of Example 1 (5.0 g), lactose (759.5 g), erythritol (200.0 g), and hydroxypropylcellulose (30.0 g) were mixed, and the mixture was added with purified water (70.0 g) and kneaded. The mixture was granulated, dried, and sieved for size adjustment. The resultant granules were mixed with magnesium stearate (5.0 g) and a flavoring agent (0.5 g) to obtain granules containing 5.0 mg of sulfate of the compound of Example 1 per 1.0 g.

Formulation Example 3

Preparation of Injection

Hydrochloride of the compound of Example 1 (60.0 mg) was dissolved in distilled water for injection according to the Japanese Pharmacopoeia (90 mL), and filled up to 100.0 mL with distilled water for injection according to the Japanese Pharmacopoeia. The resultant solution was filtered, filled into vials (5.0 mL for each vial), and lyophilized in a conventional manner, and the vials were sealed to obtain preparation for injection containing 3.0 mg of hydrochloride of the compound of Example 1 per vial. This preparation can be dissolved in physiological saline according to the Japanese Pharmacopoeia (5.0 mL), glucose injection according to the Japanese Pharmacopoeia (5%, 5.0 mL) or the like upon use, and the resultant solution can be directly administered intravenously, subcutaneously or the like. Alternatively, the resultant solution can be administered by admixing it into an injectable solution for a drip infusion to be used.

Formulation Example 4

Preparation of Suppositories

Methanesulfonate of the compound of Example 1 (150.0 mg) was mixed with a melted hot fatty suppository base (Witepsol H15, 499.85 g), and the mixture was filled into a mold (1.0 g for each suppository), and cooled to obtain suppositories containing 3.0 mg of methanesulfonate of the compound of Example 1 per each suppository.

Test Example 1

Test for 5-HT$_3$ Receptor Activating Action

The serotonin 5-HT$_3$ receptor antagonistic activity and the serotonin 5-HT$_3$ receptor activating action of the following typical compounds that fall within the benzoxazole compounds of the present invention: 2-(1-homopiperazinyl)benzoxazole (A) (compound disclosed in Japanese Patent Publication (KOKAI) No. 6-345744/1994), 5,7-dimethyl-2-(4-methyl-1-piperazinyl) benzoxazole (B), 5,7-dimethyl-2-(1-piperazinyl)benzoxazole (C), 5-chloro-7-methyl-2-(4-methyl-1-piperazinyl)benzoxazole (D), and 5-chloro-7-methyl-2-(4-methyl-1-homopiperazinyl) benzoxazole (E) (compounds disclosed in Japanese Patent Publication (KOKAI) No. 10-29987/1998), and 5-chloro-7-methyl-2-(1-piperazinyl)benzoxazole (F) (compound of Reference Example 3 of the present specification) were measured as follows. The results are shown in Table 1.

From ileum of Hartley male guinea pigs (500 g to 800 g) longitudinal muscle samples of about 20 mm were prepared. The samples were suspended at a resting tension of about 0.5 g in Magnus tubes, and isometric contraction reaction was measured. The samples were treated beforehand twice with 0.3 μM of 5-HT for 1 hour to desensitize the 5-HT$_4$ receptors, and then given with 5-HT at a concentration of 0.1 to 30 μM to examine dose-dependent contraction reaction via the 5-HT$_3$ receptors. The maximum reaction was observed at a concentration of 10 μM. The index of the 5-HT$_3$ receptor activating action, i.a., is represented as a ratio of the maximum reaction obtained by each compound relative to the maximum contraction reaction obtained with 10 μM of 5-HT, which is defined to be 1. The index of strength of binding with the 5-HT$_3$ receptor, pD$_2$, is represented with a negative logarithmic value of a concentration (molar concentration) that gave 50% maximum contraction reaction for each compound. As for the antagonistic activity of each compound against the 5-HT$_3$ receptor, inhibitory ratio was calculated, which represents a ratio of contraction obtained by applying 10 μM of 5-HT to a sample treated beforehand with 10 μM of each compound relative to the contraction obtained by applying 10 μM of 5-HT to an untreated sample.

5-HT$_3$ Receptor Activating Action Test

| Test compound | Antagonism (10 μM, %) | Activating action i.a. | pD$_2$ |
|---|---|---|---|
| Compound of Example 1 (a) | 95 | 0.12 | 7.48 |
| Compound of Example 2 | 88 | 0.36 | 6.53 |
| Compound of Example 3 | 88 | 0.08 | 6.72 |
| Compound of Example 4 | 89 | 0.07 | 7.75 |
| Compound of Example 6 | 90 | 0.35 | 5.40 |
| Compound of Example 7 | 83 | 0.31 | 5.70 |
| Compound of Example 8 | 83 | 0.55 | 6.36 |
| Compound of Example 9 | 97 | 0.13 | 7.25 |
| Compound of Example 10 | 96 | 0.09 | 7.25 |
| Compound of Example 11 | 89 | 0.14 | 7.45 |
| Compound of Example 12 | 88 | 0.05 | 6.72 |
| Compound of Example 14 | 46 | 0.13 | 5.47 |
| Compound of Example 16 | 15 | 0.10 | 5.25 |
| A | — | 0.32 | 5.77 |
| B | — | 0.62 | 6.32 |
| C | 91 | 0.12 | 7.15 |
| D | 94 | 0.27 | 6.79 |
| E | 98 | 0.17 | 7.67 |
| F | 90 | 0.14 | 7.56 |

Test Example 2

Test for Inhibitory Action for Rat Diarrhea Under Restriction Stress

Inhibitory action for rat diarrhea under restriction stress of the compound of Example 1 (b) of the present specification, hydrochloride of 5,7-dimethyl-2-(1-piperazinyl)benzoxazole (C) and hydrochloride of 5-chloro-7-methyl-2-(4-methyl-homopiperazinyl)benzoxazole (E) (compounds disclosed in Japanese Patent Publication (KOKAI) No. 10-29987/1998), and Granisetron (G) according to the method of C. L. Williams et al. [GASTROENTEROLOGY, 94, 611–621 (1988)] was determined as follows, and the results were analyzed by the nonlinear least square method. The results are shown in Table 2.

8-Week old male Wistar rats were starved from the evening of the day before the test. Each test compound was orally administered to the rats. After 30 minutes, the rats were constrained by binding of their fore-limbs and hind-limbs with wires. The rats were left in individual gages on white sheets under luminescent lamps for 3 hours. When hair near their anuses was dirty with feces, or their feces did not have solid shapes, the rats were determined to be suffered from diarrhea. The test was performed with groups of rats each consisting of 8 rats.

| Inhibition action for rat diarrhea under restriction stress | |
|---|---|
| Test compound | ED$_{50}$ value (mg/kg) |
| Compound of Example 1 (b) | 0.00025 |
| Hydrochloride of C | 0.0272 |
| Hydrochloride of E | 0.0041 |
| G | 0.025 |

Test Example 3

Effect on Large Bowel Transportation Ability of Normal Mice

Effect on large bowel transportation ability of normal mice of the compound of Example 1 (b) of the present specification, hydrochloride of 5,7-dimethyl-2-(1-piperazinyl)benzoxazole (C) and hydrochloride of 5-chloro-7-methyl-2-(4-methyl-1-homopiperazinyl)benzoxazole (E) (compounds disclosed in Japanese Patent Publication (KOKAI) No. 10-29987/1998), and Granisetron (G) according to the method of Pendleton R. G. et al. [Drug Dev. Res., 9, 241–247, (1986)] was determined as follows. The results are shown in Table 3.

Each test compound was orally administered to 5- to 7-week old ddY male mice starved for about 4 hours. After 30 minutes, one glass bead having a diameter of about 3 mm was inserted from anus into colon of each mouse, and placed at a position 3 cm distant from the anus. After the insertion of the glass bead, time (second) from the insertion to excretion of the bead from the anus was measured, and the time was used as an index of large bowel transportation ability. The test was performed by using groups of mice each consisting of 9 to 11 mice, and all of the procedures were performed under no anesthesia.

Effect on Large Bowel Transportation Ability of Normal Mice

| | Dose (mg/kg) | | | |
|---|---|---|---|---|
| Test compound | 0 | 3 | 10 | 30 |
| Compound of Example 1 (b) | 199.18 | 218.39 | 313.60 | 239.11 |
| Hydrochloride of C | 225.87 | 234.01 | 251.00 | 357.08 |
| Hydrochloride of E | 225.87 | 271.91 | 318.95 | 248.56 |
| G | 199.18 | 206.44 | 258.47 | 475.93 |

Test Example 4

Test for Metabolic Activity in Human Liver with In Vitro System

Metabolic activity in human liver of the compound of Example 1 (b) of the present specification, hydrochloride of 5,7-dimethyl-2-(1-piperazinyl)benzoxazole (C), hydrochloride of 5-chloro-7-methyl-2-(4-methyl-1-piperazinyl) benzoxazole (D), and hydrochloride of 5-chloro-7-methyl-2-(4-methyl-1-homopiperazinyl)benzoxazole (E) (compounds disclosed in Japanese Patent Publication (KOKAI) No.

10-29987/1998) was determined by using an in vitro test system utilizing human S9 fraction as follows. The results are shown in Table 4.

The test was performed in an in vitro system utilizing human liver S9 fraction in the presence of an NADPH production system described below. A reaction mixture of a total volume of 125 μL containing components at given final concentrations was prepared (50 μmol/L of test compound, 6 mmol/L of $MgCl_2.6H_2O$, 1 mmol/L of β-$NADP^+$, 10 mmol/L of glucose-6-phosphate (G-6-P), 0.7 U/mL of G-6-P dehydrogenase, 100 mmol/L of potassium phosphate (pH 7.4), 0.1 mmol/L of $EDTANa_2$, and 1 mg/mL of human liver S9), and incubated at 37 C.° for 15 minutes. The reaction was stopped by the addition of 125 μL of N,N-dimethylformamide containing a substance for internal standard. The reaction mixture was centrifuged (2,000×g, 10 minutes), and the supernatant was subjected to HPLC analysis to determine the concentration of unchanged substance. Consumed amount was calculated from the concentration of unchanged substance, and the metabolic rate was represented as activity per unit amount of protein. For the measurement of the compound of Example 1, Compounds C and E, Compound D was used as an internal standard substance. For the measurement of Compound D, a compound disclosed in Japanese Patent Publication (KOKAI) No. 10-29987/1998, 5,7-dichloro-2-(4-methyl-1-piperazinyl) benzoxazole, was used as the internal standard substance.

| Test for metabolic activity in human liver using in vitro system | |
|---|---|
| Test compound | Metabolic activity[1] |
| Compound of Example 1 (b) | N.D.[2] |
| Hydrochloride of C | 0.06 |
| Hydrochloride of D | 0.87 |
| Hydrochloride of E | 0.50 |

[1]Unit: nmol/min/mg protein
[2]N.D. means that concentration of test compound in a sample was not changed before and after the incubation.

Test Example 5

Reverse Mutation Test

A reverse mutagenicity test was performed using the compound of Example 1 (b) of the present specification, hydrochloride of 5,7-dimethyl-2-(1-piperazinyl)benzoxazole (C), hydrochloride of 5-chloro-7-methyl-2-(4-methyl-1-piperazinyl)benzoxazole (D), and hydrochloride of 5-chloro-7-methyl-2-(4-methyl-1-homopiperazinyl) benzoxazole (E) (compounds disclosed in Japanese Patent Publication (KOKAI) No. 10-29987/1998), and the compound described in Reference Example 4 of the present specification, i.e., hydrochloride of 5-chloro-7-methyl-2-(1-piperazinyl) benzoxazole (F) according to the method of T. Matsushima et al. (Noropoth K. H., Springer, Berlin-Heidelberg-New York, "Short-Term Test Systems For Detecting Carcinogens", pp. 273–285, 1980) referred by the guideline 471 of ORGANIZATION FOR ECONOMIC CO-OPERATION AND DEVELOPMENT.

As a result, the compound of Example 1 (b) of the present specification, hydrochloride of Compound C, hydrochloride of Compound D, and hydrochloride of Compound E were determined to be negative for the reverse mutagenicity, and hydrochloride of Compound F was determined to be positive for the reverse mutagenicity.

Example 6

Toxicity Test

The compound of Example 1(b) of the present specification suspended in distilled water was orally administered to 7-week old male mice (five mice). The compound of Example 1 (b) gave no death of the animal at a dose of 300 mg/kg.

INDUSTRIAL APPLICABILITY

The benzoxazole derivatives of the present invention are 5-$HT_3$ receptor partial activators having both strong 5-$HT_3$ receptor antagonistic activity and 5-$HT_3$ receptor activating action (see, Test Example 1), and they showed strong inhibitory effect against diarrhea induced by restriction stress (see, Test Example 2). In addition, the compounds of the present invention do not affect the large bowel transportation ability of normal mice (see, Test Example 3). Moreover, the compounds of the present invention are hardly metabolized in human livers (see, Test Example 4), and show low reverse mutagenicity (see, Test Example 5).

From the facts mentioned above, it can be concluded that 5-$HT_3$ receptor partial activators containing the compounds of the present invention as an active ingredient are useful as agents for preventive or therapeutic treatment of irritable bowel syndrome, digestive tract functional disorder, or diarrhea.

What is claimed is:

1. 5-Chloro-2-(1-homopiperazinyl)-7-methylbenzoxazole or a salt thereof.

2. A pharmaceutical composition which comprises, as an active ingredient, an effective amount of a substance selected from the group consisting of the compound according to claim 1, a pharmaceutically acceptable salt thereof, a hydrate thereof, and a solvate thereof.

3. A method for the manufacture of the pharmaceutical composition according to claim 2, which comprises mixing the substance selected from the group consisting of 5-chloro-2-(1-homopiperazinyl)-7-methylbenzoxazole, a pharmaceutically acceptable salt thereof, a hydrate thereof and a solvate thereof, with a pharmaceutical carrier.

4. A method for therapeutic treatment of condition of irritable bowel syndrome or digestive tract functional disorder, or condition of diarrhea, which comprises a step of administering to a mammal including human a therapeutically effective amount of a substance selected from the group consisting of the compound according to claim 1, a pharmaceutically acceptable salt thereof, a hydrate thereof, and a solvate thereof.

5. A serotonin 5-$HT_3$ receptor antagonistic agent or partial activator for therapeutic treatment of condition of irritable bowel syndrome or digestive tract functional disorder, or condition of diarrhea, comprising as an active ingredient, an effective amount of a substance selected from the group consisting of 5-chloro-2-(1'-homopiperazinyl)-7-methylbenzoxazole, a pharmaceutically acceptable salt thereof, a hydrate thereof, and a solvate thereof.

* * * * *